(12) United States Patent  (10) Patent No.: US 9,259,160 B2
Watson et al.  (45) Date of Patent: Feb. 16, 2016

(54) SYSTEMS AND METHODS FOR DETERMINING WHEN TO MEASURE A PHYSIOLOGICAL PARAMETER

(75) Inventors: James N. Watson, Fife (GB); Paul Stanley Addison, Midlothian (GB); Rakesh Sethi, Vancouver (CA); Keith Manning, Lothian (GB)

(73) Assignee: Nellcor Puritan Bennett Ireland, Galway (IE)

( * ) Notice: Subject to any disclaimer, the term of this patent is extended or adjusted under 35 U.S.C. 154(b) by 619 days.

(21) Appl. No.: 12/957,538

(22) Filed: Dec. 1, 2010

(65) Prior Publication Data

US 2012/0143067 A1    Jun. 7, 2012

(51) Int. Cl.
*A61B 5/02*    (2006.01)
*A61B 5/021*    (2006.01)
*A61B 5/00*    (2006.01)

(52) U.S. Cl.
CPC .......... *A61B 5/02108* (2013.01); *A61B 5/7239* (2013.01); *A61B 2560/0223* (2013.01)

(58) Field of Classification Search
USPC ................................................. 600/483, 485
See application file for complete search history.

(56) References Cited

U.S. PATENT DOCUMENTS

| | | |
|---|---|---|
| 3,835,840 A | 9/1974 | Mount |
| 4,561,447 A | 12/1985 | Kawamura et al. |
| 4,676,253 A | 6/1987 | Newman et al. |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle et al. |
| 5,103,831 A | 4/1992 | Niwa |
| 5,105,815 A | 4/1992 | Hall et al. |

(Continued)

FOREIGN PATENT DOCUMENTS

| | | |
|---|---|---|
| EP | 0443267 | 8/1991 |
| EP | 0755221 | 1/1997 |

(Continued)

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

(Continued)

*Primary Examiner* — Navin Natnithithadha
*Assistant Examiner* — Michael R Bloch
(74) *Attorney, Agent, or Firm* — Shvarts & Leiz LLP

(57) ABSTRACT

Systems and methods are provided for determining when to update a blood pressure measurement. The value of a physiological metric may be monitored and compared to a reference value. A patient monitoring system may compute a difference between a monitored metric and a reference value, and compare the difference to a threshold value to determine whether to update a blood pressure measurement. The threshold value may be constant or variable, and may depend on the monitored metric.

20 Claims, 8 Drawing Sheets

(56) References Cited

U.S. PATENT DOCUMENTS

| | | |
|---|---|---|
| 5,111,817 A | 5/1992 | Clark et al. |
| 5,119,824 A | 6/1992 | Niwa |
| 5,131,400 A | 7/1992 | Harada |
| 5,163,328 A | 11/1992 | Holland |
| 5,165,416 A * | 11/1992 | Shinoda et al. ............... 600/485 |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A * | 7/1996 | Kaspari et al. ................ 600/485 |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,842,975 A | 12/1998 | Illyés et al. |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,921,936 A | 7/1999 | Inukai et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,050,951 A * | 4/2000 | Friedman et al. ............ 600/485 |
| 6,067,462 A | 5/2000 | Diab |
| 6,083,171 A | 7/2000 | Ono et al. |
| 6,095,987 A | 8/2000 | Shmulewitz |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,331,162 B1 | 12/2001 | Mitchell |
| 6,332,867 B1 | 12/2001 | Chen et al. |
| 6,350,242 B1 | 2/2002 | Doten et al. |
| 6,371,921 B1 | 4/2002 | Caro |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,984 B1 | 5/2003 | Turcott |
| 6,561,986 B2 | 5/2003 | Baura |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,648,828 B2 * | 11/2003 | Friedman et al. .............. 600/506 |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,893,401 B2 | 5/2005 | Chen et al. |
| 6,929,610 B2 | 8/2005 | Forstner |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |
| 7,376,238 B1 | 5/2008 | Rivas et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,455,643 B1 | 11/2008 | Li et al. |

(56) References Cited

U.S. PATENT DOCUMENTS

| | | | |
|---|---|---|---|
| 7,481,772 | B2 | 1/2009 | Banet |
| 7,485,095 | B2 | 2/2009 | Shusterman |
| 7,769,436 | B1 | 8/2010 | Boileau et al. |
| 2002/0095090 | A1* | 7/2002 | Caro et al. .................. 600/485 |
| 2004/0210625 | A1* | 10/2004 | Bodin et al. .................. 709/201 |
| 2005/0038332 | A1 | 2/2005 | Saidara et al. |
| 2005/0148885 | A1 | 7/2005 | Tweed et al. |
| 2005/0251344 | A1 | 11/2005 | Appel et al. |
| 2005/0261594 | A1 | 11/2005 | Banet |
| 2006/0009700 | A1 | 1/2006 | Brumfield et al. |
| 2006/0063992 | A1 | 3/2006 | Yu et al. |
| 2006/0063993 | A1 | 3/2006 | Yu et al. |
| 2006/0079945 | A1 | 4/2006 | Libbus |
| 2006/0122517 | A1 | 6/2006 | Banet et al. |
| 2006/0206021 | A1 | 9/2006 | Diab |
| 2006/0217614 | A1 | 9/2006 | Takala et al. |
| 2006/0217628 | A1 | 9/2006 | Huiku |
| 2006/0241975 | A1 | 10/2006 | Brown |
| 2006/0285736 | A1 | 12/2006 | Brown |
| 2006/0287603 | A1 | 12/2006 | Bartnik et al. |
| 2007/0027375 | A1 | 2/2007 | Melker et al. |
| 2007/0055163 | A1 | 3/2007 | Asada et al. |
| 2007/0066910 | A1 | 3/2007 | Inukai et al. |
| 2007/0083093 | A1 | 4/2007 | Diab |
| 2007/0118045 | A1 | 5/2007 | Naghavi et al. |
| 2007/0142730 | A1 | 6/2007 | Laermer et al. |
| 2007/0225582 | A1 | 9/2007 | Diab et al. |
| 2007/0249467 | A1 | 10/2007 | Hong et al. |
| 2008/0015451 | A1 | 1/2008 | Hatib et al. |
| 2008/0030468 | A1 | 2/2008 | Ali et al. |
| 2008/0033305 | A1 | 2/2008 | Hatib et al. |
| 2008/0097175 | A1 | 4/2008 | Boyce et al. |
| 2008/0132798 | A1 | 6/2008 | Hong et al. |
| 2008/0194932 | A1 | 8/2008 | Ayers et al. |
| 2008/0214903 | A1 | 9/2008 | Orbach |
| 2008/0214942 | A1 | 9/2008 | Oh et al. |
| 2008/0242955 | A1 | 10/2008 | Uutela et al. |
| 2009/0048497 | A1 | 2/2009 | Keren |
| 2009/0326395 | A1 | 12/2009 | Watson |
| 2010/0016746 | A1 | 1/2010 | Hampton et al. |
| 2010/0222653 | A1 | 9/2010 | Siejko et al. |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 03-225268 | 12/2003 |

OTHER PUBLICATIONS

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. S11-S14.

Fitchett, D., Bouthier, JD, Simon, A. CH., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994, pp. 1-446.

Fung, YC, Biomechanics: Circulation, 2nd Edition, New York, Springer, 1997, pp. 1-571.

Geddes, LA, Handbook of Blood Pressure Measurement, Clifton, New Jersey, Humana Press, 1991, pp. 1-168.

Millasseau, Sandrine C, Guigui, Franck G, Kelly, Ronan P., Prasad, Krishna, Cockcroft, John R., Ritter, James M., Chowienczyk, Philip J., "Noninvasive Assessment of the Digital Volume Pulse: Comparison with the Peripheral Pressure Pulse, Hypertension," vol. 36, No. 6, Dec. 2000, pp. 952-956.

Moyle, John TB, Hahn, Cew, Adams, Anthony P, Pulse Oximetry, Revised Edition, London, BMJ, 1998, pp. 1-140.

Nara, Andrew R., Burns, Michael P., Downs, W. Gregory, Blood Pressure, Redmond, Washington, SpaceLabs, 1989, pp. 1-109.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990, pp. 1-456.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, Feb. 1991, pp. 39-54.

Young, Christopher C., Mark, Jonathan B., White, William, Debree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

SYSTEMS AND METHODS FOR DETERMINING WHEN TO MEASURE A PHYSIOLOGICAL PARAMETER

SUMMARY

Continuous non-invasive blood pressure (CNIBP) monitoring systems allow a patient's blood pressure to be tracked continuously, unlike standard occlusion cuff techniques, and without the hazards of invasive arterial lines. In some embodiments, systems may use multiple pulse oximetry type sensors located at multiple body sites on a patient to measure photoplethysmograph (PPG) signals. The resulting multiple PPG signals may be compared against each other to estimate the patient's blood pressure. When the locations of two sensors are at different distances from the heart or along different paths from the heart (e.g., at the finger and forehead), a differential pulse transit time (DPTT) may be determined. A DPTT may represent the difference in the arrival times of a portion of a cardiac wave between the two locations, and may be determined by comparing corresponding fiducial points in the two PPG signals (e.g., a maximum, minimum, or a notch). In some techniques, two DPTTs are determined in order to calculate multiple physiological parameters, such as systolic and diastolic blood pressure. These DPTTs may be determined during different portions of the PPG signal representing different physiological occurrences. For example, one DPTT may be determined when the cardiovascular system is in a systolic state and a second DPTT may be determined when the cardiovascular system is in a diastolic state.

During physiological monitoring of a patient with a patient monitoring system, physiological events may occur. For example, one or more physiological signals or metrics derived thereof may deviate from a reference value or threshold. It may be desirous in some instances to generate an event marker to demarcate the occurrence of the physiological event. For example, a metric may be monitored and compared to a reference metric. If the metric differs from the reference metric by a particular value, a patient monitoring system may respond with a suitable action such as, for example, storing an event marker, triggering an alarm, storing data, updating a measurement, or other suitable function.

Systems and methods are provided herein for generating and storing event markers. Event markers may be stored in a suitable memory device, and recalled at a desired time. Values of one or more metrics associated with one or more physiological signals (e.g., PPG signals) may be monitored by a patient monitoring system and compared with reference or threshold values. If it is determined by the patient monitoring system that the value of the monitored metric differs from a reference value or threshold by a particular value, the patient monitoring system may respond with a corresponding action.

In some embodiments, a patient monitoring system may compare a monitored metric value to one or more threshold or reference values. Threshold values may be stored values, metric values computed at a particular time, user defined values, any other suitable values, or any combination thereof. In some embodiments, a threshold value may depend at least in part on the relative difference between a monitored metric value and a reference value. For example, depending on whether a difference (e.g., between a monitored metric value and a reference value) is positive or negative, one or two respective threshold value may be used. In some embodiments, a threshold value may be proportional to the value of the monitored metric.

The methods and systems of the present disclosure will be illustrated with reference to the monitoring of a physiological signal (which may be a PPG signal). However, it will be understood that the disclosure is not limited to monitoring physiological signals and is usefully applied within a number of signal monitoring settings.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
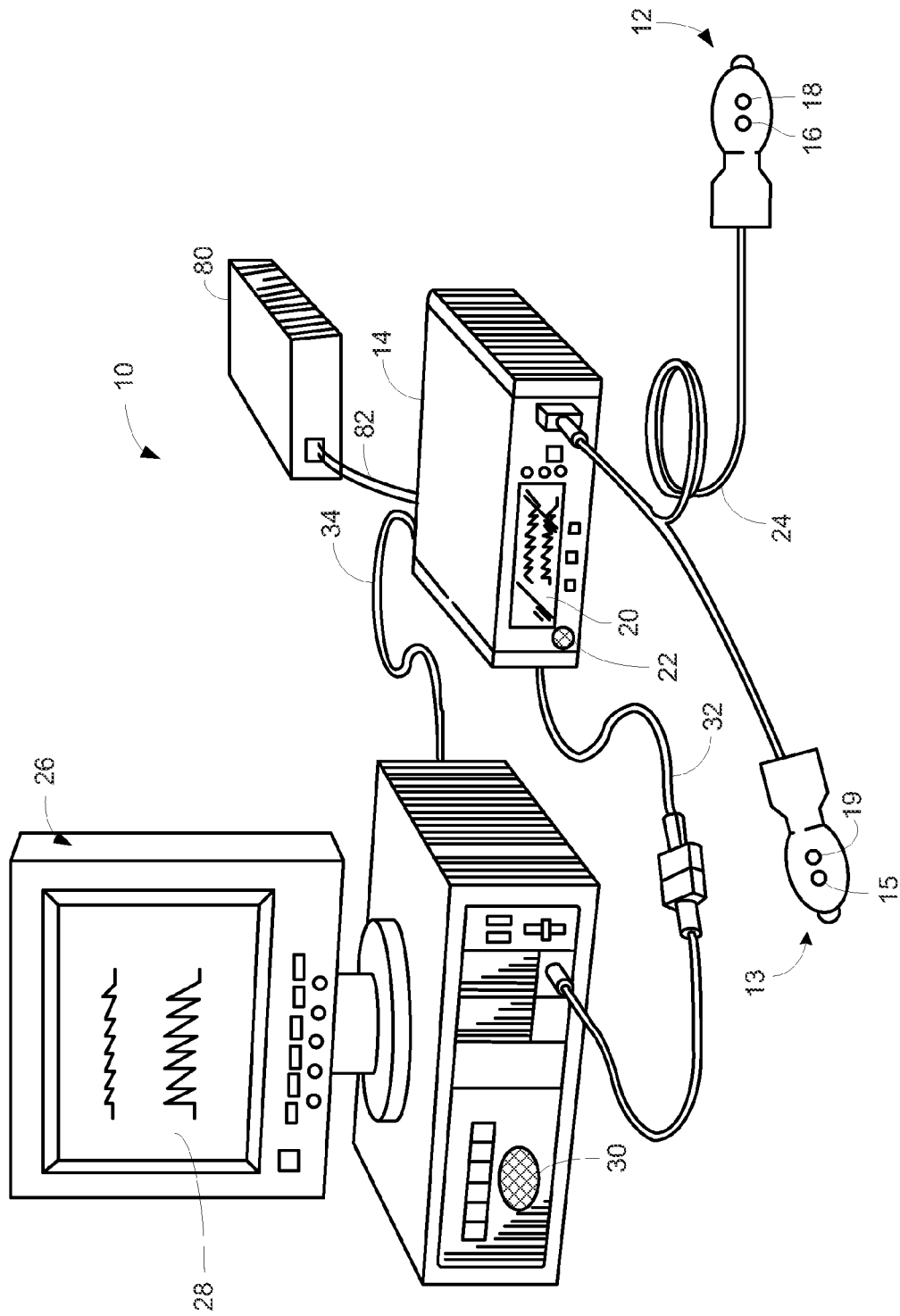
FIG. 1 shows an illustrative patient monitoring system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Patient monitoring systems may also measure and display additional physiological parameters, such as a patient's pulse rate and blood pressure.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t) = I_O(\lambda)\exp(-(s\beta_o(\lambda) + (1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_o, \beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_O - (s\beta_O + (1-s)\beta_r)l. \quad (2)$$

2. Eq. 2 is then differentiated with respect to time to yield $$\frac{d\log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{\frac{d\log I(\lambda_R)}{dt}}{\frac{d\log I(\lambda_{IR})}{dt}} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \quad (5)$$

5. Note that, in discrete time, the following approximation can be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{\frac{dI}{dt}}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} = \quad (11)$$

-continued $$\frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R,$$

which defines a cluster of points whose slope of y versus x will give R when $$x = [I(t_2, \lambda_{IR}) - I(t_1, \lambda_{IR})]I(t_1, \lambda_R), \quad (12)$$

and $$y = [I(t_2, \lambda_R) - I(t_1, \lambda_R)]I(t_1, \lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In an embodiment, sensor unit 12 may be part of a continuous, non-invasive blood pressure (CNIBP) monitoring system and/or an oximeter. Sensor unit 12 may include an emitter 16 for emitting light at one or more wavelengths into a patient's tissue. A detector 18 may also be provided in sensor 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units, such as sensor unit 13, which may take the form of any of the embodiments described herein with reference to sensor unit 12. For example, sensor unit 13 may include emitter 15 and detector 19. Sensor unit 13 may be the same type of sensor unit as sensor unit 12, or sensor unit 13 may be of a different sensor unit type than sensor unit 12. Sensor units 12 and 13 may be capable of being positioned at two different locations on a subject's body; for example, sensor unit 12 may be positioned on a patient's forehead, while sensor unit 13 may be positioned at a patient's fingertip.

Sensor units 12 and 13 may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include a plurality of sensors forming a sensor array in lieu of either or both of sensor units 12 and 13. Each of the sensors of a sensor array may be a complementary metal oxide semiconductor (CMOS) sensor. Alternatively, each sensor of an array may be charged coupled device (CCD) sensor. In an embodiment, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more of sensor units 12 and 13 in accordance with the systems and techniques disclosed herein. It is understood that any number of sensors measuring any number of physiological signals may be used to determine physiological information in accordance with the techniques described herein.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as in a sensor designed to obtain pulse oximetry data from a patient's forehead.

In an embodiment, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood pressure, blood oxygen saturation) based at least in part on data relating to light emission and detection received from one or more sensor units such as sensor units 12 and 13. In an alternative embodiment, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In an embodiment, the monitor 14 includes a blood pressure monitor. In alternative embodiments, the system 10 includes a stand-alone blood pressure monitor in communication with the monitor 14 via a cable or a wireless network link.

In an embodiment, sensor unit 12 may be communicatively coupled to monitor 14 via a cable 24. However, in other embodiments, a wireless transmission device (not shown) or the like may be used instead of or in addition to cable 24.

In the illustrated embodiment, system 10 includes a multi-parameter patient monitor 26. The monitor 26 may include a cathode ray tube display, a flat panel display (as shown) such as a liquid crystal display (LCD) or a plasma display, or may include any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation generated by monitor 14 (referred to as an "SpO$_2$" measurement), pulse rate information from monitor 14 and blood pressure from monitor 14 on display 28. Multi-parameter patient monitor 26 may include a speaker 30.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14 via a cable 82, a battery, or by a conventional power source such as a wall outlet, may include any suitable signal calibration device. Calibration device 80 may be communicatively coupled to monitor 14 via cable 82, and/or may communicate wirelessly (not shown). In other embodiments, calibration device 80 is completely integrated within monitor 14. For example, calibration device 80 may take the form of any invasive or non-invasive blood pressure monitoring or measuring system used to generate reference blood pressure measurements for use in calibrating a CNIBP monitoring technique as described herein. Such calibration devices may include, for example, an aneroid or mercury sphygmomanometer and occluding cuff, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference signal measurements obtained from some other source (e.g., an external invasive or non-invasive physiological measurement system).

Calibration device 80 may also access reference signal measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. The reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle or a different periodic cycle. Reference blood pressure measurements may be generated when recalibration is triggered.

Figure 2:
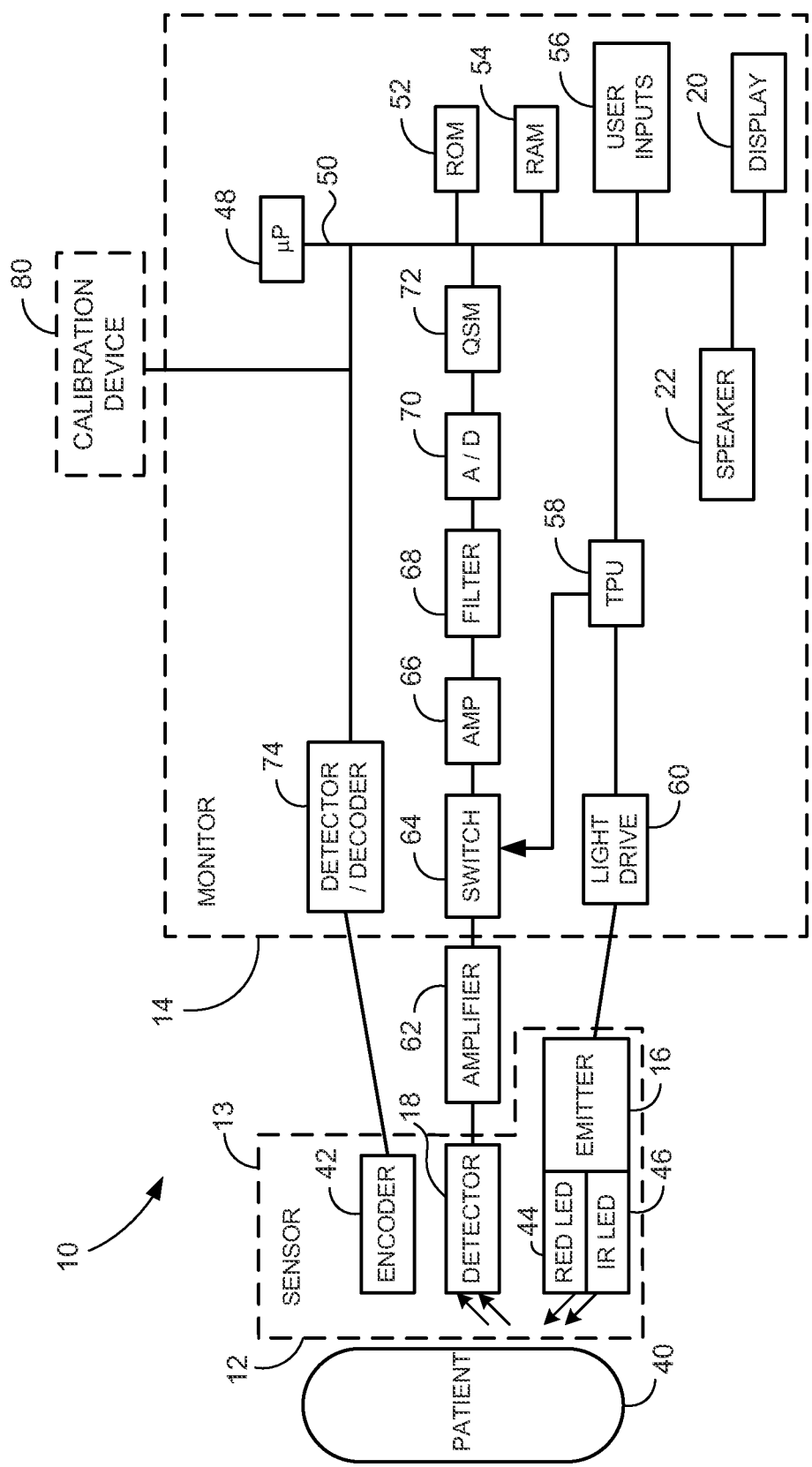
FIG. 2 is a block diagram of the illustrative patient monitoring system of FIG. 1 coupled to a patient in accordance with an embodiment.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2. Because sensor units 12 and 13 may include similar components and functionality, only sensor unit 12 will be discussed in detail for ease of illustration. It will be understood that any of the concepts, components, and operation discussed in connection with sensor unit 12 may be applied to sensor unit 13 as well (e.g., emitter 16 and detector 18 of sensor unit 12 may be similar to emitter 15 and detector 19 of sensor unit 13). It will be noted that patient monitoring system 10 may include one or more additional sensor units or probes, which may take the form of any of the embodiments described herein with reference to sensor units 12 and 13 (FIG. 1). These additional sensor units included in system 10 may take the same form as sensor unit 12, or may take a different form. In an embodiment, multiple sensors (distributed in one or more sensor units) may be located at multiple different body sites on a patient.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In one embodiment, the Red wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a Red light while a second emits only an IR light. In another example, the wavelengths of light used are selected based on the specific location of the sensor.

It will be understood that, as used herein, the term "light" may refer to energy produced by radiation sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which, for example, blood pressure and other measurements may be determined based at least in part on the signal or signals received at sensor unit 12. For example, some pulse oximetry sensors rely on equations to relate an area under a pulse of a photoplethysmograph (PPG) signal to determine blood pressure. These equations may contain coefficients that depend upon a patient's physiological characteristics as stored in encoder 42. Encoder 42 may, for instance, be a coded resistor which stores values corresponding to the type of sensor unit 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor unit 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 fills up. In one embodiment, there may be multiple separate parallel paths having components equivalent to amplifier 66, filter 68, and/ or A/D converter 70 for multiple light wavelengths or spectra received.

In an embodiment, microprocessor 48 may determine the patient's physiological parameters, such as SpO$_2$, pulse rate, and/or blood pressure, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals or otherwise identify noise components in order to prevent them from affecting measurements of physiological parameters derived from the sensor signals.

Pulse oximeters, in addition to providing other information, can be utilized for continuous non-invasive blood pressure monitoring. As described in Chen et al., U.S. Pat. No. 6,599,251, the entirety of which is incorporated herein by reference, PPG and other pulse signals obtained from multiple probes can be processed to calculate the blood pressure of a patient. In particular, blood pressure measurements may be derived based on a comparison of time differences between certain components of the pulse signals detected at each of the respective probes. As described in U.S. patent application Ser. No. 12/242,238, filed on Sep. 30, 2008 and entitled "Systems and Methods For Non-Invasive Blood Pressure Monitoring," the entirety of which is incorporated herein by reference, blood pressure can also be derived by processing time delays detected within a single PPG or pulse signal obtained from a single pulse oximeter probe. In addition, as described in U.S. patent application Ser. No. 12/242,867, filed on Sep. 30, 2008 and entitled "Systems and Methods For Non-Invasive Continuous Blood Pressure Determination," the entirety of which is incorporated herein by reference, blood pressure may also be obtained by calculating the area under certain portions of a pulse signal. Finally, as described in U.S. patent application Ser. No. 12/242,862, filed on Sep. 30, 2008 and entitled "Systems and Methods For Maintaining Blood Pressure Monitor Calibration," the entirety of which is incorporated herein by reference, a blood pressure monitoring device may be recalibrated in response to arterial compliance changes.

As described above, some CNIBP monitoring techniques utilize two probes or sensors positioned at two different locations on a subject's body. The elapsed time, T, between the arrivals of corresponding points of a pulse signal at the two locations may then be determined using signals obtained by the two probes or sensors. The estimated blood pressure, p, may then be related to the elapsed time, T, by $$p = a + b \cdot \ln(T) \tag{14}$$

where a and b are constants that may be dependent upon the nature of the subject and the nature of the signal detecting devices. Other suitable equations using an elapsed time between corresponding points of a pulse signal may also be used to derive an estimated blood pressure measurement.

In an embodiment, Eq. 14 may include a non-linear function which is monotonically decreasing and concave upward in T in a manner specified by the constant parameters (in addition to or instead of the expression of Eq. 14). Eq. 14 may be used to calculate an estimated blood pressure from the time difference T between corresponding points of a pulse signal received by two sensors or probes attached to two different locations of a subject.

In an embodiment, constants a and b in Eq. 14 above may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

In an embodiment, the calibration may include performing calculations mathematically equivalent to $$a = c_1 + \frac{c_2(P_0 - c_1)}{\ln(T_0) + c_2} \quad (15)$$

and $$b = \frac{P_0 - c_1}{\ln(T_0) + c_2} \quad (16)$$

to obtain values for the constants a and b, where $c_1$ and $c_2$ are parameters that may be determined, for example, based on empirical data.

In an embodiment, the calibration may include performing calculations mathematically equivalent to $$a = P_0 - (c_3 T_0 + c_4)\ln(T_0) \quad (17)$$

and $$b = c_3 T_0 + c_4 \quad (18)$$

where a and b are first and second parameters and $c_3$ and $c_4$ are parameters that may be determined, for example, based on empirical data.

Parameters $c_1$, $c_2$, $c_3$, and $c_4$ may be predetermined constants empirically derived using experimental data from a number of different patients. A single reference blood pressure reading from a patient, including reference blood pressure $P_0$ and elapsed time $T_0$ from one or more signals corresponding to that reference blood pressure, may be combined with such inter-patient data to calculate the blood pressure of a patient. The values of $P_0$ and $T_0$ may be referred to herein as a calibration point. According to this example, a single calibration point may be used with the predetermined constant parameters to determine values of constants a and b for the patient (e.g., using Eqs. 15 and 16 or 17 and 18). The patient's blood pressure may then be calculated using Eq. 14. Recalibration may be performed by collecting a new calibration point and recalculating the constants a and b used in Eq. 14. Calibration and recalibration may be performed using calibration device 80 (FIG. 1).

In an embodiment, multiple calibration points from a patient may be used to determine the relationship between the patient's blood pressure and one or more PPG signals. This relationship may be linear or non-linear and may be extrapolated and/or interpolated to define the relationship over the range of the collected recalibration data. For example, the multiple calibration points may be used to determine values for parameters $c_1$ and $c_2$ or $c_3$ and $c_4$ (described above). These determined values will be based on information about the patient (intra-patient data) instead of information that came from multiple patients (inter-patient data). As another example, the multiple calibration points may be used to determine values for parameters a and b (described above). Instead of calculating values of parameters a and b using a single calibration point and predetermined constants, values for parameters a and b may be empirically derived from the values of the multiple calibration points. As yet another example, the multiple calibration points may be used directly to determine the relationship between blood pressure and PPG signals. Instead of using a predefined relationship (e.g., the relationship defined by Eq. 14), a relationship may be directly determined from the calibration points.

Additional examples of continuous and non-invasive blood pressure monitoring techniques are described in Chen et al., U.S. Pat. No. 6,566,251, which is hereby incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body.

Figure 3:
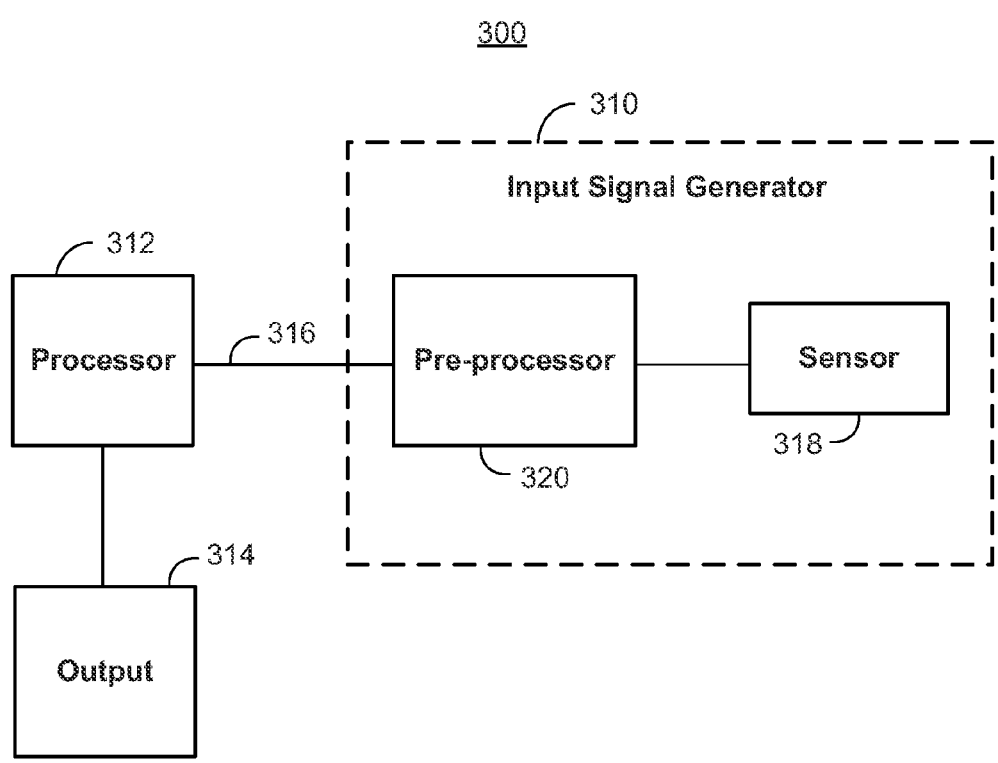
FIG. 3 is a block diagram of an illustrative signal processing system in accordance with an embodiment.

FIG. 3 is an illustrative signal processing system 300 in accordance with an embodiment that may implement the non-invasive blood pressure techniques described herein. In this embodiment, input signal generator 310 generates an input signal 316. As illustrated, input signal generator 310 may include pre-processor 320 coupled to sensor 318, which may provide input signal 316. In an embodiment, pre-processor 320 may be an oximeter and input signal 316 may be a PPG signal. In an embodiment, pre-processor 320 may be any suitable signal processing device and input signal 316 may include one or more PPG signals and one or more other physiological signals, such as an electrocardiogram (ECG) signal. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing operations to the signal generated by sensor 318. For example, pre-processor 320 may apply a predetermined set of processing operations to the signal provided by sensor 318 to produce input signal 316 that can be appropriately interpreted by processor 312, such as performing A/D conversion. Pre-processor 320 may also perform any of the following operations on the signal provided by sensor 318: reshaping the signal for transmission, multiplexing the signal, modulating the signal onto carrier signals, compressing the signal, encoding the signal, and filtering the signal.

In an embodiment, signal 316 may include PPG signals at one or more frequencies, such as a Red PPG signal and an IR PPG signal. In an embodiment, signal 316 may include signals measured at one or more sites on a patient's body, for example, a patient's finger, toe, ear, arm, or any other body site. In an embodiment, signal 316 may include multiple types of signals (e.g., one or more of an ECG signal, an EEG signal, an acoustic signal, an optical signal, a signal representing a blood pressure, and a signal representing a pulse rate). Signal 316 may be any suitable biosignal or signals, such as, for example, electrocardiogram, electroencephalogram, electrogastrogram, electromyogram, pulse rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

In an embodiment, signal 316 may be coupled to processor 312. Processor 312 may be any suitable software, firmware, hardware, or combination thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may, for example, be configured of analog electronic components. Processor 312 may perform the calculations associated with the information determination techniques of the present disclosure as well as the calculations associated with any calibration of processing system 300 or other auxiliary functions. For example, processor 312 may locate one or more fiducial points in one or more signals, determine one or more DPTTs, and compute one or more of a systolic blood pressure, a diastolic blood pressure and a mean arterial pressure. Processor 312 may perform any suitable signal processing of signal 316 to filter signal 316, such as any suitable band-pass filtering, adaptive filtering, closed-loop filtering, any other suitable filtering, and/or any combination thereof. Processor 312 may also receive input signals from additional sources (not shown). For example, processor 312 may receive an input signal containing information about treatments provided to the patient. Additional input signals may be used by processor 312 in any of the calculations or operations it performs in accordance with processing system 300.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store data corresponding to blood pressure monitoring, including current blood pressure calibration values, blood pressure monitoring calibration thresholds, and patient blood pressure history. In an embodiment, processor 312 may store physiological measurements or previously received data from signal 316 in a memory device for later retrieval. In an embodiment, processor 312 may store calculated values, such as a systolic blood pressure, a diastolic blood pressure, a blood oxygen saturation, a differential pulse transit time, a fiducial point location or characteristic, or any other calculated values, in a memory device for later retrieval.

Processor 312 may be coupled to a calibration device. This coupling may take any of the forms described above with reference to calibration device 80 within system 10. For example, the calibration device may be a stand-alone device that may be in wireless communication with processor 312, or may be completely integrated with processor 312.

Processor 312 may be coupled to a calibration device that may generate, or receive as input, reference measurements for use in calibration calculations. This coupling may occur through a recalibration signal transmitted via a wired or wireless communications path. In an embodiment, processor 312 is capable of transmitting a command to calibration device 80 to initiate a recalibration procedure.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor units 12 and 13 (FIGS. 1 and 2) and monitor 14 (FIGS. 1 and 2) and processor 312 may be implemented as part of monitor 14 (FIGS. 1 and 2). In some embodiments, portions of system 300 may be configured to be portable. For example, all or part of system 300 may be embedded in a small, compact object carried with or attached to the patient (e.g., a watch, other piece of jewelry, or a cellular telephone). In such embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In such embodiments, a wireless transceiver (not shown) may also be included in system 300 to enable wireless communication with other components of system 10. For example, pre-processor 320 may output signal 316 over BLUETOOTH, 802.11, WiFi, WiMax, cable, satellite, Infrared, or any other suitable transmission scheme. In an embodiment, a wireless transmission scheme may be used between any communicating components of system 300.

Pre-processor 320 or processor 312 may determine the locations of pulses within a periodic signal 316 (e.g., a PPG signal) using a pulse detection technique. For ease of illustration, the following pulse detection techniques will be described as performed by processor 312, but any suitable processing device (e.g., pre-processor 320) may be used to implement any of the techniques described herein.

Figure 4:
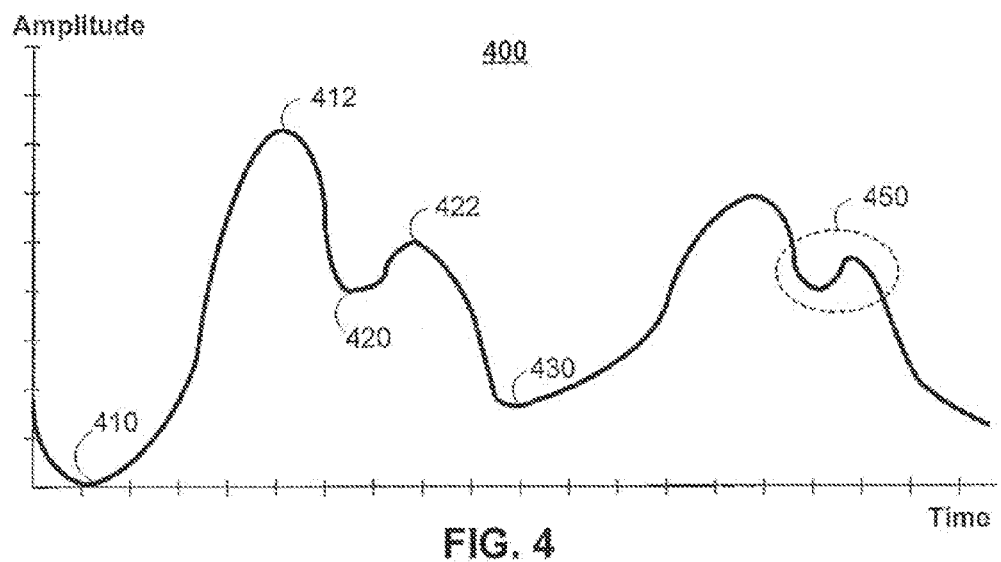
FIG. 4 is an illustrative signal which may be analyzed in accordance with an embodiment.

An illustrative PPG signal 400 is depicted in FIG. 4. Processor 312 may receive PPG signal 400, and may identify local minimum point 410, local maximum point 412, local minimum point 420, and local maximum point 422 in the PPG signal 400. Processor 312 may pair each local minimum point with an adjacent maximum point. For example, processor 312 may pair points 410 and 412 to identify one segment, points 412 and 420 to identify a second segment, points 420 and 422 to identify a third segment and points 422 and 430 to identify a fourth segment. The slope of each segment may be measured to determine whether the segment corresponds to an upstroke portion of the pulse (e.g., a positive slope) or a downstroke portion of the pulse (e.g., a negative slope) portion of the pulse. A pulse may be defined as a combination of at least one upstroke and one downstroke. For example, the segment identified by points 410 and 412 and the segment identified by points 412 and 420 may define a pulse.

According to an embodiment, PPG signal 400 may include a dichrotic notch 450 or other notches (not shown) in different sections of the pulse (e.g., at the beginning (referred to as an ankle notch), in the middle (referred to as a dichrotic notch), or near the top (referred to as a shoulder notch)). Processor 312 may identify notches and either utilize or ignore them when detecting the pulse locations. In some embodiments, processor 312 may compute the second derivative of the PPG signal to find the local minima and maxima points and may use this information to determine a location of, for example, a dichrotic notch. Additionally, processor 312 may interpolate between points in signal 316 or between points in a processed signal using any interpolation technique (e.g., zero-order hold, linear interpolation, and/or higher-order interpolation techniques). Some pulse detection techniques that may be performed by processor 312 are described in more detail in co-pending, commonly assigned U.S. patent application Ser. No. 12/242,908, filed Sep. 30, 2008 and entitled "SYSTEMS AND METHODS FOR DETECTING PULSES IN A PPG SIGNAL," which is incorporated by reference herein in its entirety.

In some embodiments, a patient monitoring system may receive one or more physiological signals associated with a patient. Particular physiological signal values, changes in values, or both, may indicate that a physiological event has occurred (e.g., an increase in the BP of the patient over a threshold) or that a suitable event may be desired (e.g., a patient monitoring system recalibration). In some embodiments, metrics (e.g., mathematical characterizations) may be derived at least in part from one or more physiological signals. Particular metric values, changes in values, or both, may indicate that a physiological event has occurred (e.g., an increase in BP) or that a suitable event may be desired (e.g., a patient monitoring system calibration). In some embodiments, signals, metrics, or both, may be monitored by a patient monitoring system to determine whether physiological events have occurred. As used herein, the term "physiological event" may refer to any defined physiological change, condition, or both of a monitored subject (e.g., blood pressure or blood pressure change exceeds a threshold). A physiological event may also refer to a defined change in a particular morphology or feature of a particular physiological signal (e.g., slope of a PPG exceeds a threshold).

Event markers may be generated by a patient monitoring system to demarcate or otherwise distinguish the occurrence of physiological events. In some embodiments, event markers may be generated based at least in part on monitored values (e.g., signals, metrics), threshold values, reference values, stored values, any other suitable information or data, or any combination thereof. Event markers may be displayed, audibly announced, stored (e.g., recorded), transmitted, or otherwise be made available by a patient monitoring system.

In some embodiments, a patient monitoring system may make one or more determinations regarding physiological events. A patient monitoring system may make determinations such as, for example, whether a physiological event has occurred, whether to trigger a response to a physiological event, whether to update a particular measurement, any other suitable determination, or any combination thereof. For example, a patient monitoring system may determine that a calibration is desired based at least in part on a monitored metric value.

Metrics may be used to characterize or otherwise describe a physiological signal. Metrics may include suitable signal values, signal morphologies, output values from suitable operations performed on a signal or other metric, any other suitable mathematical characterizations, or any suitable combinations thereof. For example, metrics may include pulse wave area (PWA), geometric centroid of a pulse wave, rate of change computed at one or more points of a time series (e.g., derivative of any suitable order of a signal), statistics of a signal (e.g., mean, moment of any suitable order, regression parameters), offset of a signal from a baseline, interval of portion of a signal (e.g., length of upstroke), relative position of a fiducial point of a signal (e.g., dichrotic notch position), any other suitable metric or change thereof, or any suitable combinations thereof. For example, in some embodiments, the skewness (e.g., the standardized third central moment) of a pulse wave may be monitored. Metrics may include mathematical manipulations of other metrics such as, for example, the value of an integral of a portion of a blood pressure measurement time series, the skewness of a derivative of a PPG signal, or any other suitable mathematical manipulations. In some embodiments, metrics may be computed from averaged, filtered, scaled, or otherwise processed physiological signals. For example, a derivative may be computed from a suitable ensemble average of pulse waves.

The term "pulse wave" as used herein refers to a portion of a PPG signal corresponding to a physiological pulse.

Figure 5:
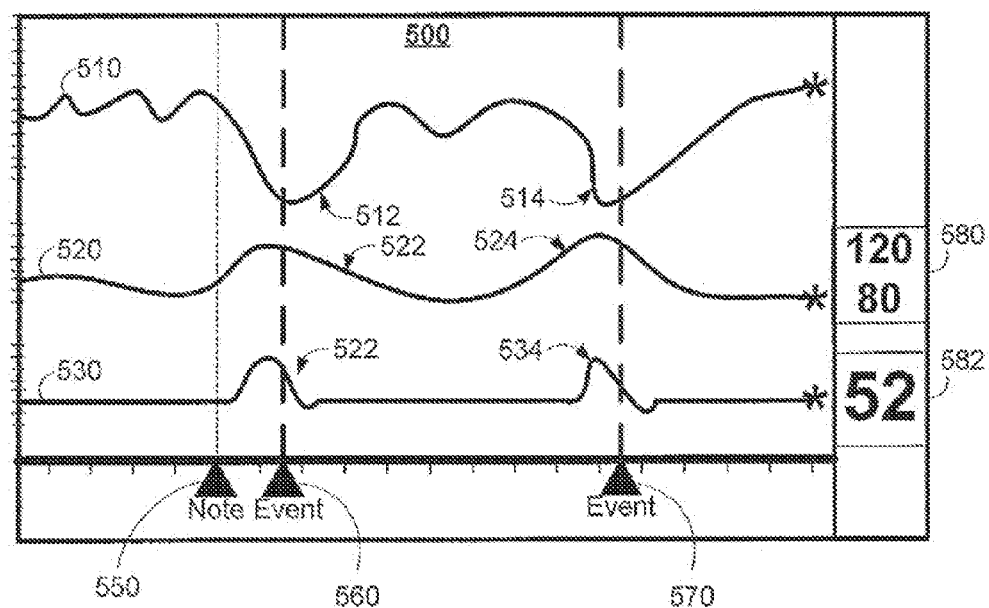
FIG. 5 is an illustrative display including event markers in accordance with an embodiment.

Shown in FIG. 5 is illustrative display 500 including event markers 560 and 570 in accordance with some embodiments. Display 500 may be displayed by any suitable display device including, for example, a patient monitor, a display screen (e.g., a computer monitor screen, a television screen, a projection screen), a screen on a portable device (e.g., a personal communication device, handheld monitoring device), any other suitable display device, or any suitable combination thereof. In some embodiments, display 500 may show time series of any suitable signals, physiological metrics, values derived at least in part thereof, or any combination thereof. For example, display 500 may include time series of DPTT (e.g., time series 510 of FIG. 5), blood pressure (e.g., time series 520 of FIG. 5), pulse rate (e.g., time series 530 of FIG. 5), $SPO_2$, one or more PPG signals, any other suitable metric derived from a signal (e.g., a PPG signal, an ECG signal), and other suitable physiological metric, or any suitable combination thereof. The term "time series" as used herein refers to a collection of metric values, each associated with a particular time. For example a time series may include blood pressure measurement values taken at regular time intervals for any suitable time domain.

In some embodiments, illustrative display 500 may include annotations, such as those illustratively shown by note 550, event marker 560, and event marker 570. For example, a user may input to a patient monitoring system note 550 to represent a time when an action was performed by the user, such as administering a drug to a patient.

In some embodiments, illustrative display 500 may include one or more numeric displays or "readouts" of signal or metric values. For example, display 500 may include blood pressure readout 580, pulse rate readout 582, any other suitable readouts, or combinations thereof. In some embodiments, a patient monitoring system may display a readout of a particular value of a metric in response to user input (e.g., notes, user selection), event markings, signal sampling, any other stimuli, or any combination thereof.

As shown in FIG. 5, time series 510, 520 and 530 undergo a change directly following note 550. For example, following note 550, time series 510 decreases in value and then increases in value, forming feature 512. The patient monitoring system may generate event marker 560 to denote changes associated with any of features 512, 522, 532, or combinations thereof.

As shown in FIG. 5, time series 510, 520 and 530 undergo another change following event marker 560. For example, following event marker 560, time series 510 decreases in value and then increases in value, forming feature 514. The patient monitoring system may generate event marker 570 to denote changes associated with any of features 514, 524, 534, or combinations thereof. In some embodiments, the patient monitoring system may determine that features 514, 524, and 534 correspond to features 512, 522, and 532, respectively, and that the physiological events associated with event markers 560 and 570 are the same.

In some embodiments, a patient monitoring system may store one or more signal values, one or more metric values, one or more time values, physiological event type, physiological event information, any other suitable information, or any combination thereof when generating an event marker (e.g., event markers 560 or 570).

Figure 6:
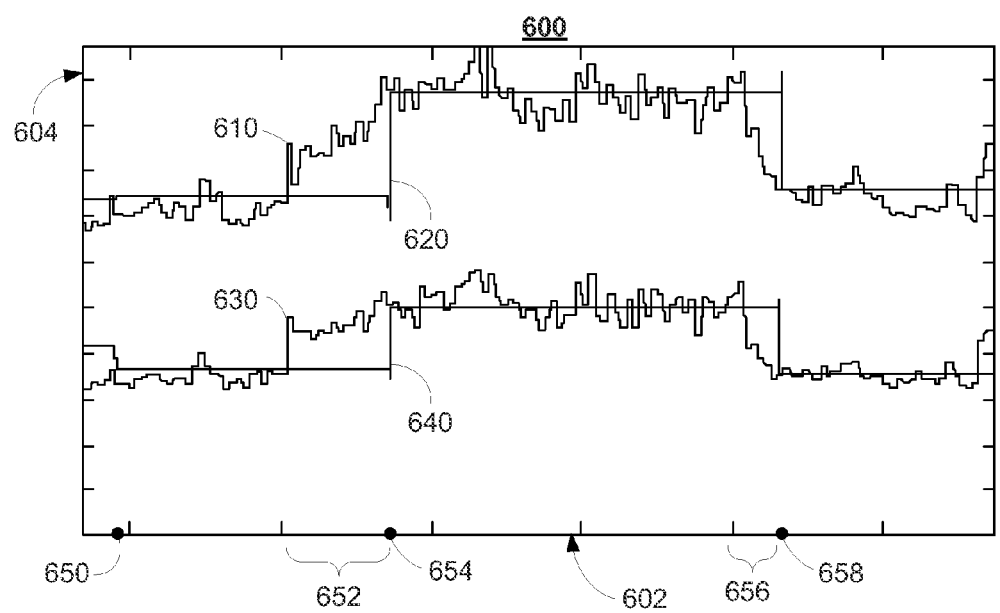
FIG. 6 is an illustrative graph of several blood pressure time series in accordance with an embodiment.

Shown in FIG. 6 is illustrative graph 600 including blood pressure time series 610, 620, 630 and 640 in accordance with an embodiment. Graph 600 may include abscissa 602 which may be a time variable (e.g., minutes), and ordinate 604 which may be blood pressure measurement value (e.g., mmHg). Time series 610 and 630 may correspond to systolic and diastolic blood pressure measurements, respectively, based at least in part on signals from two suitable CNIBP devices (e.g., PPG sensors). Time series 620 and 640 may correspond to systolic and diastolic blood pressure measurements, respectively, of an NIBP device (e.g., arterial line blood pressure sensor), for example. Event markers may be generated at times 650, 654, and 658, and may represent changes in blood pressure.

In some embodiments, a patient monitoring system may monitor signals, metrics, or both, associated with one or more CNIBP devices, an arterial line BP sensor, any other suitable physiological signal, or any combinations thereof. The patient monitoring system may display a particular BP value associated with the arterial line BP sensor signal at a particular time. The patient monitoring system may monitor one or more BP values derived at least in part from the CNIBP devices. The patient monitoring system may determine that a physiological event has occurred based at least in part on the monitored BP values, the patient monitoring system may, for example, store an event marker, trigger a response (e.g., update the displayed NIBP value, calibrate the CNIBP devices), any other suitable function, or any combination thereof.

For example, between times 650 and 654, the values of both time series 620 and 640 are observed to be constant in time. In this same time interval, values of both time series 610 and 630 are observed to remain roughly constant early in the interval and then increase substantially over time window 652. In some embodiments, a patient monitoring system may determine that a physiological event has occurred based on the value of times series 610 and 630. For example, if the difference between values of time series 610 and 620 is greater than a threshold, the patient monitoring system may determine that a physiological event has occurred (e.g., blood pressure increase). If the patient monitoring system determines that a particular physiological event has occurred (e.g., an increase in blood pressure), the patient monitoring system may update the value of time series 620, generate event marker at time 654, or both. For example, in some embodiments, at time 654 the patient monitoring system may sample the signal from arterial line BP sensor, compute one or more BP values, and update the BP measurements.

Between times 654 and 658, the values of both time series 620 and 640 are observed to be constant in time. In this same time interval, values of both time series 610 and 630 are observed to remain roughly constant early in the interval and then decrease substantially over time window 656. In some embodiments, a patient monitoring system may determine that a physiological event has occurred based on the value of times series 610 and 630. For example, if the difference between values of time series 610 and 620 is greater than a threshold, the patient monitoring system may determine that a physiological event has occurred (e.g., blood pressure decrease). If the patient monitoring system determines that a particular physiological event has occurred (e.g., a decrease in blood pressure), the patient monitoring system may update the value of time series 620, generate event marker 658, or both. For example, in some embodiments, the patient monitoring system may update the value of time series 620 associated with the arterial line BP sensor.

In some embodiments, values associated with time series 620 and 640 may be displayed by a patient monitoring system to increase the time scale over which the displayed BP measurements changes, as compared to the time scale over which time series 610 and 630 change.

Figure 7:
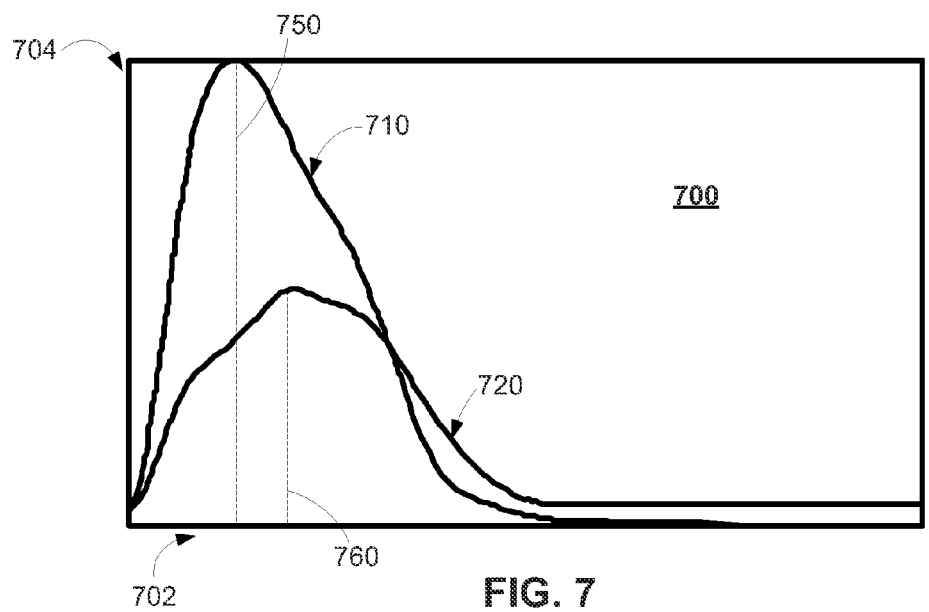
FIG. 7 is an illustrative graph of portions of PPG signals in accordance with an embodiment.

Shown in FIG. 7 is illustrative graph 700 including time series 710 and 720 in accordance with an embodiment. Graph 700 may include abscissa 702 which may be a time variable (e.g., seconds), and ordinate 704 which may be a signal value. Time series 710 and 720 may represent ensemble averages of portions of a PPG signal corresponding to physiological pulses. Time series 710 may represent an ensemble average of portions of the PPG signal collected while systolic pressure is in the top quartile. Time series 720 may represent an ensemble average of portions of the PPG signal collected while systolic pressure is in the bottom quartile. A patient monitor may be able to distinguish between time series 710 and 720 by, for example, computing respective metric values associated with the two time series and comparing the metric values. For example, a patient monitoring system may distinguish between the peak heights, full widths at half maximum (FWHM), integral, centroids of the pulse waves, any other suitable metrics, or any combination thereof based at least in part on time series 710 and 720.

In some embodiments, one or more metrics such as peak height may be used by the patient monitoring system as a threshold value. For example, a patient monitoring system may store the peak heights (e.g., a shown by dotted lines 750 and 760) of time series 710 and 720 as upper and lower threshold values, respectively. During monitoring of one or more PPG signals, if the patient monitoring system determines that a physiological event is occurring such as the peak value of the monitored signal is greater than the upper threshold value, or less than the lower threshold value, the patient monitoring system may, for example, generate an event marker. A patient monitoring system may use any suitable metric values, signal values, thresholds, any other suitable values, or combination thereof to determine whether a physiological event has occurred or is occurring.

In some embodiments, thresholds may be used for comparison with monitored values, computed values, or both. In some embodiments, for example, a monitored metric value may be compared with threshold values. In some embodiments, for example, a difference between a monitored metric value and a reference value may be compared with threshold values. Thresholds may include constant values (e.g., fixed values), variables values (e.g., dynamic thresholds), or both.

In some embodiments, thresholds may be proportional to a monitored metric value. For example, a threshold may be proportional to a BP measurement. As the BP measurement increases, the threshold value increases. In some embodiments, a proportional threshold may allow greater deviation of a monitored metric value from a reference value before the threshold is exceeded.

In some embodiments, the value of a threshold may depend on the relative magnitudes of a monitored metric value and a reference value. For example, if a BP measurement of a patient is relatively low, a particular reference value may be determined. If the monitored BP measurement is less than the reference value, the threshold may be smaller (e.g., absolute value of the threshold is smaller) than if the monitored BP measurement is greater than the reference value. The difference between the monitored metric value and reference value may be negative when the monitored metric value is less than the reference value. The threshold associated with a negative difference may be distinct from the threshold associated with a positive difference. In some embodiments, a relative threshold may allow greater deviation of a monitored metric value from a reference value if the monitored metric value is greater than (or less than in some embodiments) the reference value.

Figure 8:
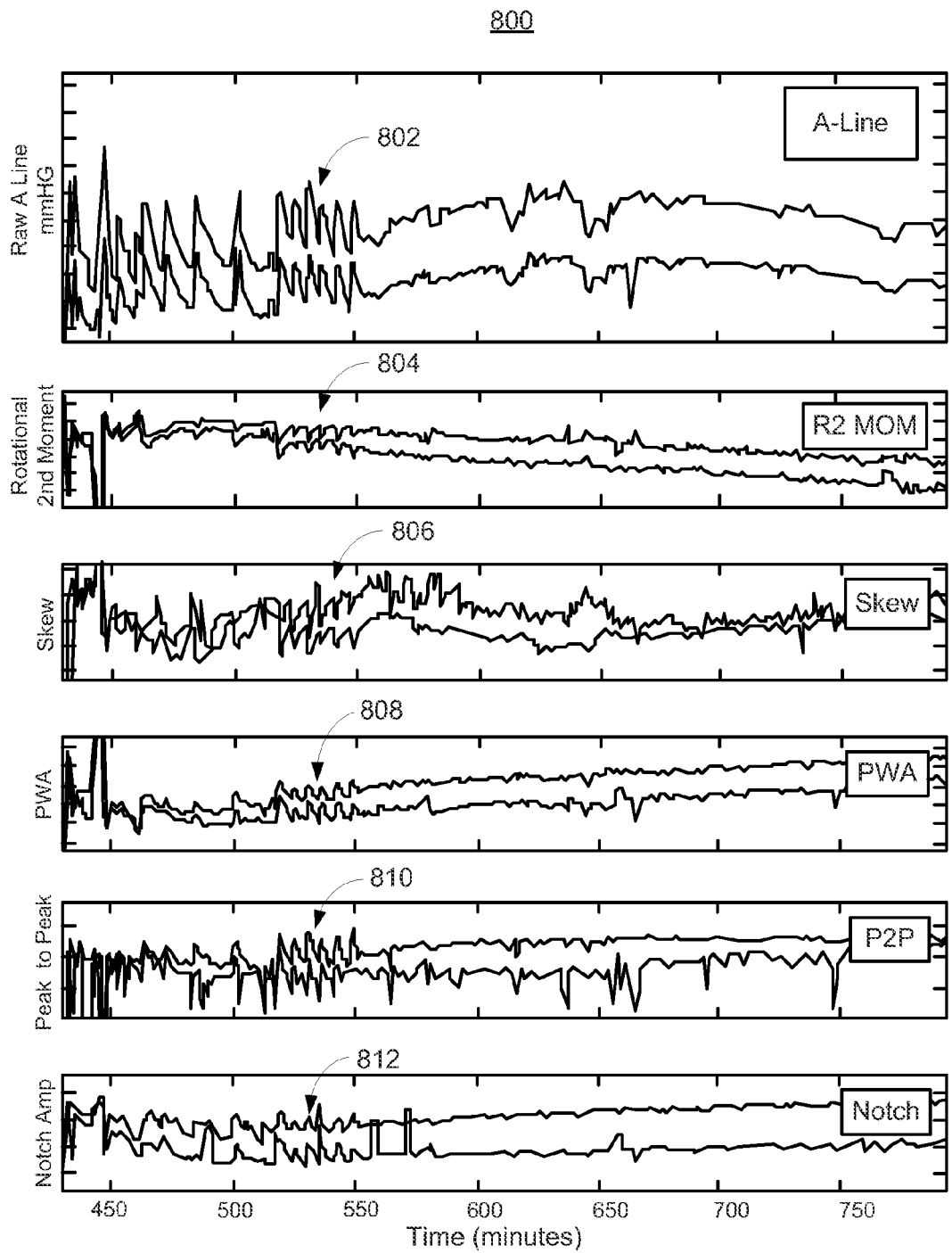
FIG. 8 is an illustrative graph of several signal parameters in accordance with an embodiment.

Shown in FIG. 8 is illustrative panel 800 showing several time series of metrics in accordance with an embodiment. The time series included in panel 800 include systolic and diastolic BP ("A-Line" of FIG. 8), PPG pulse wave rotation moments for two PPG signals ("R2 MOM" of FIG. 800), PPG pulse wave skew for two PPG signals ("Skew" of FIG. 800), PPG pulse wave area (e.g., integral) for two PPG signals ("PWA" of FIG. 800), PPG pulse wave peak to peak amplitude for two PPG signals ("P2P" of FIG. 800), and dichrotic notch amplitude ("Notch" of FIG. 800). The abscissa of the graphs of panel 800 is shown in units of minutes. The illustrative ordinate values are arbitrary, and are not necessarily consistent for the different time series of panel 800.

In some embodiments, the behavior of the time series of metrics such as those shown in FIG. 8 may show similar characteristics. For example, as shown by time series regions 802, 804, 806, 808, 810, and 812 show similar oscillatory behavior at similar times. The similar oscillatory behavior may indicate that monitoring one or more particular metrics may allow physiological events to be distinguished.

Figure 9:
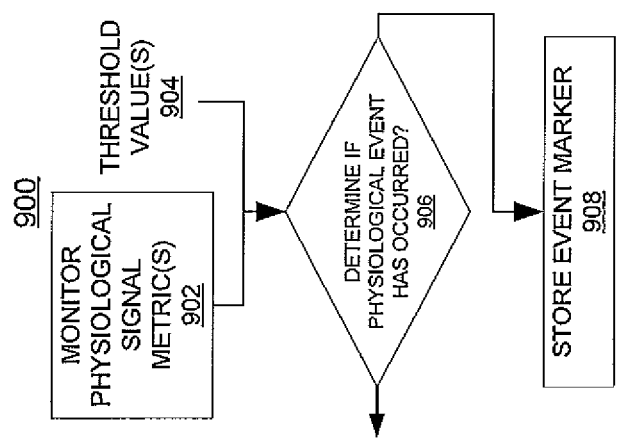
FIG. 9 is a flow diagram of illustrative steps for storing an event marker in accordance with an embodiment.

Shown in FIG. 9 is flow diagram 900 of illustrative steps for storing an event marker in accordance with an embodiment. Illustrative step 902 may include monitoring at least one metric derived at least in part from one or more physiological signals (e.g., PPG signals) received by a patient monitoring system (e.g., patient monitoring system 10 of FIG. 1). Illustrative step 906 may include determining whether a physiological event has occurred. In some embodiments, illustrative step 906 may include receiving one or more threshold values. Illustrative determination step 908 may include storing an event marker.

Illustrative step 902 of FIG. 9 may include monitoring any suitable type of physiological signal such as, for example, a PPG signal, ECG signal, any other suitable physiological signal, any metric derived thereof, or any combinations thereof. Step 902 may include sampling, computing, averaging, storing, updating, displaying, any other suitable functions which may be performed to monitor a metric associated with a physiological signal. For example, in some embodiments, a patient monitoring system may sample one or more PPG signals, and compute one or more metric values such as pulse rate, blood pressure, signal morphology, DPTT, or other metrics or combinations thereof, derived at least in part from the one or more PPG signals.

Illustrative step 906 of FIG. 9 may include determining whether a physiological event has occurred based at least in part on a monitored metric value (e.g., a monitored metric of illustrative step 902) and at least in part on one or more threshold values (e.g., threshold values 904). A patient monitoring system may compute a difference between, for example, a monitored metric value and a threshold value. In some embodiments, the threshold value may be a metric value determined at a different time. In some embodiments, a patient monitoring system may compare a difference between a monitored metric value and a threshold value to a stored difference. In some embodiments, a patient monitoring system may determine the type of physiological event (e.g., low blood pressure, increased pulse rate) that has occurred based at least in part on the monitored metric value, the threshold value, differences thereof, or any combination thereof.

Illustrative step 908 of FIG. 9 may include storing an event marker corresponding to a physiological event which may be determined to have occurred. In some embodiments, step 908 may include displaying, audibly announcing (e.g., beeping, generating one or more audible words), storing (e.g., recorded), transmitting, any other suitable function, or any combination thereof, information associated with the physiological event that was determined to have occurred. For example, in some embodiments, step 908 may include a patient monitoring system storing one or more physiological signal values, metric values, differences, any other suitable values, or any combination thereof based at least in part on the physiological event that was determined to have occurred.

In some embodiments, a patient monitoring system may determine at step 906 that a physiological event has not occurred. The patient monitoring system may determine that a physiological event has not occurred based at least in part on one or more monitored metric values, one or more threshold values, any other suitable values, or any combination thereof. If it is determined that a physiological event has not occurred, for example, the patient monitoring system may perform step 902 (e.g., repeat step 902).

Figure 10:
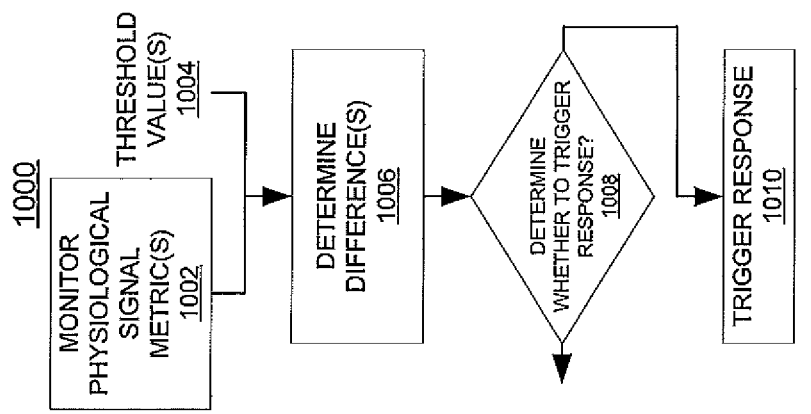
FIG. 10 is a flow diagram of illustrative steps for triggering a response to a measured difference in accordance with an embodiment.

Shown in FIG. 10 is flow diagram 1000 of illustrative steps for triggering a response to a measured difference in accordance with an embodiment. Illustrative step 1002 may include monitoring at least one metric derived at least in part from one or more physiological signals (e.g., PPG signals) received by a patient monitoring system (e.g., patient monitoring system 10 of FIG. 1). Illustrative step 1006 may include determining one or more differences. In some embodiments, illustrative step 1006 may include receiving one or more threshold values. Illustrative step 1008 may include determining whether to trigger one or more responses. Illustrative determination step 1010 may include triggering one or more responses.

Illustrative step 1002 of FIG. 10 may include monitoring any suitable type of physiological signal such as, for example, a PPG signal, ECG signal, any other suitable physiological signal, or any combinations thereof. Step 1002 may include sampling, computing averaging, storing, updating, displaying, any other suitable functions which may be performed to monitor a metric associated with a physiological signal. For example, in some embodiments, a patient monitoring system may sample one or more PPG signals, and compute one or more metric values such as pulse rate, blood pressure, signal morphology, DPTT, or other metrics or combinations thereof, derived at least in part from the one or more PPG signals.

Illustrative step 1006 of FIG. 10 may include determining one or more differences based at least in part on a monitored metric value (e.g., a monitored metric of illustrative step 1002) and at least in part on one or more threshold values (e.g., threshold values 1004). In some embodiments, a patient monitoring system may compute a difference between, for example, a monitored metric value and a threshold value. In some embodiments, a patient monitoring system may compare (e.g., compute a difference between) a difference between a monitored metric value and a threshold value to a stored difference (e.g., a second threshold value). In some embodiments, the threshold value may be a metric value determined at a different time.

Illustrative step 1008 of FIG. 10 may include determining whether to trigger a response based at least in part on a difference (e.g., the difference of step 1006). In some embodiments, a patient monitoring system may determine the type of response to trigger (e.g., update BP measurement, recalibration, alarm) based at least in part on the monitored metric value, the threshold value, differences thereof, or any combination thereof. In some embodiments, the patient monitoring system may recall or access (e.g., traverse a decision tree) a database of responses (e.g., stored in ROM 52) in which may be triggered. In some embodiments, the patient monitoring system may trigger a particular response depending on the computed difference. For example, the patient monitoring system may trigger an alarm if a difference is relatively large, or may trigger storage of an event marker if the difference is relatively small.

Illustrative step 1010 of FIG. 10 may include triggering a response to one or more determined differences. In some embodiments, step 1010 may include triggering, for example, an alarm, data storage (e.g., one or more signal values, one or metric values, one or more time values), an update of a metric value (e.g., update a displayed metric value), a recalibration, any other suitable function, or any combination thereof. For example, in some embodiments, step 1010 may include a patient monitoring system performing a NIBP (e.g., an inflatable cuff device) measurement in response to a difference between a monitored BP measurement and a threshold value.

For example, a patient monitoring system may monitor a blood pressure measurement derived at least in part from two PPG sensors suitably arranged on a patient. The patient monitoring system may compute a difference between the monitored blood pressure measurement and a threshold value. If the difference exceeds a second threshold, the patient monitoring system may determine that an alarm is to be triggered. The patient monitoring system may then record or sound an alarm notification in response to the low blood pressure measurement.

In some embodiments, a patient monitoring system may determine at step 1008 not to trigger a response. The patient monitoring system may determine not to trigger a response based at least in part on one or more monitored metric values, one or more threshold values, any other suitable values, or any combination thereof. If it is determined not to trigger a response, for example, the patient monitoring system may perform (e.g., repeat) step 1002, step 1006, any other suitable steps, or any combination thereof.

Figure 11:
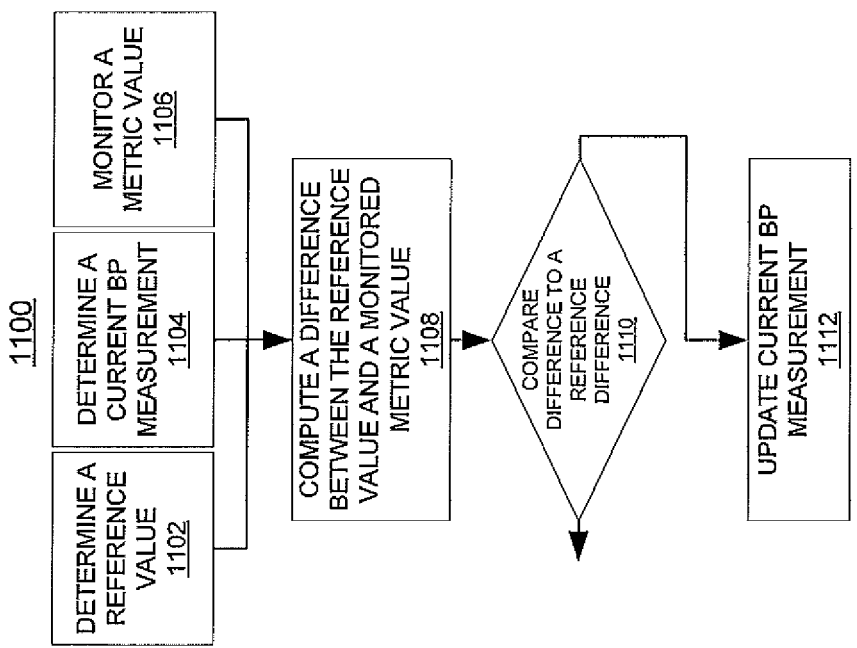
FIG. 11 is a flow diagram of illustrative steps for updating a blood pressure measurement in accordance with an embodiment.

Shown in FIG. 11 is flow diagram 1100 of illustrative steps for updating a blood pressure measurement in accordance with an embodiment. Illustrative step 1102 may include determining a reference value. Illustrative step 1104 may include determining a current BP measurement. Illustrative step 1106 may include monitoring at least one metric derived at least in part from one or more physiological signals (e.g., PPG signals) received by a patient monitoring system (e.g., patient monitoring system 10 of FIG. 1). Illustrative step 1108 may include computing a difference based at least in part on a reference metric value and a monitored metric value. In some embodiments, illustrative step 1110 may include comparing a difference which may be based at least in part on a reference metric value and a monitored metric value to a reference difference. Illustrative step 1112 may include updating a current BP measurement.

Illustrative step 1102 of FIG. 11 may include determining a reference value. A reference value may be any associated with any suitable signal value, metric value, any other suitable value, or any combination thereof. For example in some embodiments, a reference value may be a particular DPTT value computed at a particular time. Step 1104 may include recalling a reference value from memory (e.g., ROM 52), computing a reference value based at least in part on one or more physiological signals (e.g., PPG signals), computing a reference value based at least in part on one or more metrics (e.g., a DPTT value), any other suitable function, or any combination thereof.

Illustrative step 1104 of FIG. 11 may include determining a reference BP measurement. In some embodiments, the reference BP measurement may be based at least in part on the reference value of step 1102. For example, in some embodiments, the reference value may be a DPTT value determined at a particular time. The patient monitoring system may determine a reference BP measurement based at least in part on the DPTT value.

Illustrative step 1106 of FIG. 11 may include monitoring any suitable type of physiological signal such as, for example, a PPG signal, ECG signal, any other suitable physiological signal, any metric derived thereof, or any combinations thereof. Step 1106 may include sampling, computing, averaging, storing, updating, displaying, any other suitable functions which may be performed to monitor a metric associated with a physiological signal, or any combination thereof. For example, in some embodiments, a patient monitoring system may sample one or more PPG signals, and compute one or more metric values such as pulse rate, blood pressure, signal morphology, DPTT, or other metrics or combinations thereof, derived at least in part from the one or more PPG signals.

Illustrative step 1108 of FIG. 11 may include computing one or more differences based at least in part on a monitored metric value (e.g., a monitored metric of illustrative step 1106) and at least in part on one or more reference values (e.g., reference value of step 1102). In some embodiments, a patient monitoring system may compute a difference between, for example, a monitored metric value and a reference value.

Illustrative step 1110 of FIG. 11 may include comparing one or more differences to one or more reference differences. In some embodiments, a patient monitoring system may compare a difference between a reference value (e.g., reference value of step 1102) and a monitored metric value (e.g., a monitored metric value of illustrative step 1106) to a reference value. For example, in some embodiments, a patient monitoring system may compare the difference between a reference DPTT value and a monitored DPTT value to a reference DPTT difference.

In some embodiments, a patient monitoring system may compare (e.g., compute a difference between) a difference between a monitored metric value and a reference value to a threshold value. In some embodiments, the threshold value may be a metric value determined at a different time.

In some embodiments, a patient monitoring system may determine at step 1110 not to update the current BP measurement. The patient monitoring system may determine not to update the current BP measurement based at least in part on one or more monitored metric values, one or more threshold values, any other suitable values, differences thereof, or any combination thereof. If it is determined not update the current BP measurement, for example, the patient monitoring system may perform (e.g., repeat) step 1102, step 1104, step 1106, step 1108, any other suitable steps, or any combination thereof.

Illustrative step 1112 of FIG. 11 may include updating the current BP measurement. In some embodiments, step 1112 may include, for example, updating a displayed BP measurement, a recalibration of a suitable device (e.g., NIBP device, CNIBP device), any other suitable function, or any combination thereof. For example, in some embodiments, step 1112 may include a patient monitoring system performing a NIBP (e.g., an inflatable cuff device) measurement.

For example, a patient monitoring system may determine a reference DPTT value and a reference BP measurement based at least in part on the reference DPTT value. In some embodiments, the patient monitoring system may display the current BP measurement. The patient monitoring system may monitor a DPTT value derived at least in part from two PPG sensors suitably arranged on a patient. The patient monitoring system may compute a difference between the monitored DPTT value and the reference DPTT value. If the difference exceeds a reference difference, the patient monitoring system may update the current BP measurement (e.g., update the displayed current BP measurement).

Figure 12:
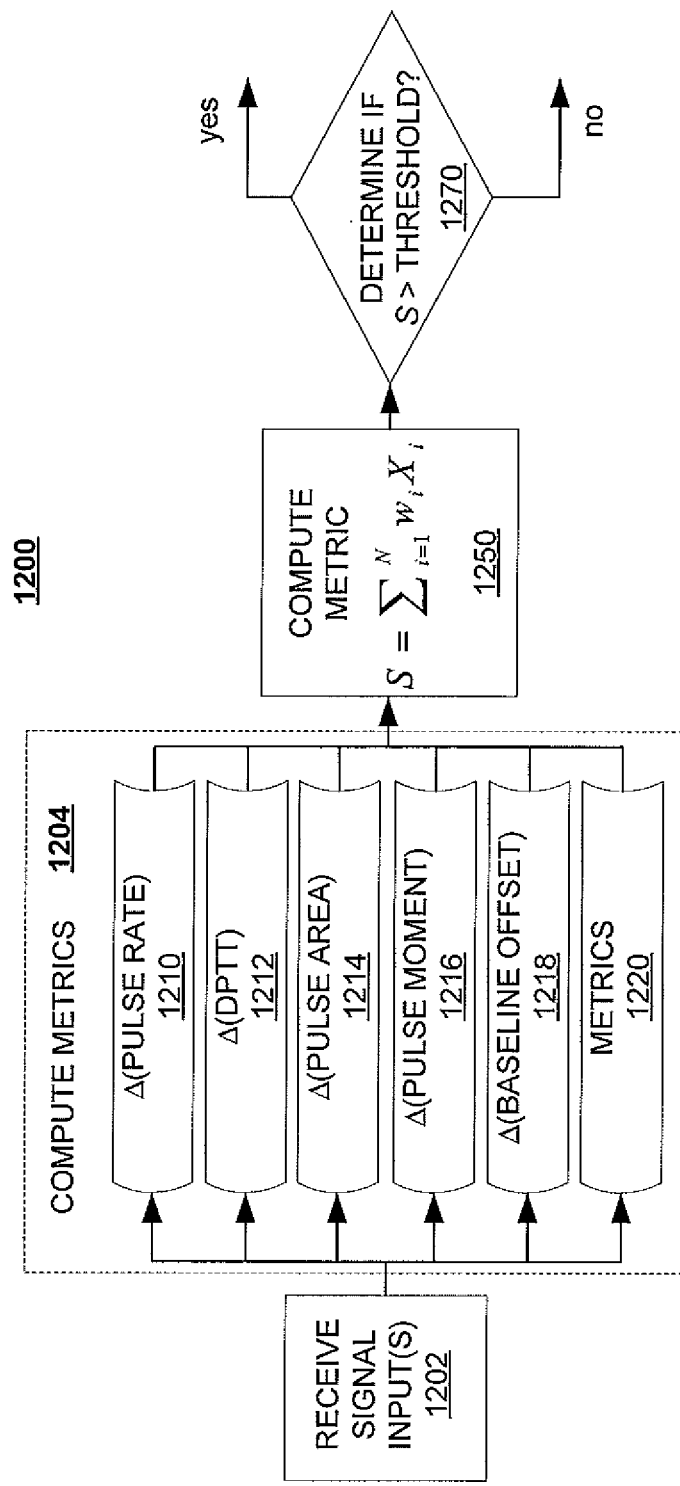
FIG. 12 is a flow diagram of illustrative steps for determining a monitoring system response in accordance with an embodiment.

Shown in FIG. 12 is flow diagram 1200 of illustrative steps for determining a monitoring system response in accordance with an embodiment. Illustrative step 1202 may include a patient monitoring system receiving one or more physiological signals (e.g., PPG signals). Illustrative step 1204 may include computing metrics based at least in part on two or more received physiological signals. Illustrative step 1250 may include computing a composite metric (e.g., a weighted sum) based at least in part on one or more other metrics. Illustrative step 1270 may include determining if the composite metric is greater than a threshold value.

Illustrative step 1202 of FIG. 12 may include receiving any suitable type of physiological signal inputs such as, for example, two PPG signals. Step 1202 may include sampling, averaging, storing, updating, displaying, any other suitable functions which may be performed along with receiving a physiological signal, or any combination thereof.

Illustrative step 1204 of FIG. 12 may include computing metrics, or changes thereof, based at least in part on, for example, two received PPG signals. For example, step 1204 may include a patient monitoring system computing changes in pulse rate 1210, DPTT 1212, pulse wave area 1214, pulse moment 1216 (e.g., of any suitable order), PPG signal offset 1218, any other suitable metrics 1220, or any combination thereof. Changes in metrics may be determined by computing a difference between each metric at a particular time, and a reference value. The reference value may be a computed metric value from a different time (e.g., value at the last time a calibration was performed), a stored value, or any other suitable value.

Illustrative step 1250 of FIG. 12 may include computing a composite metric. In some embodiments, as shown in step 1250 of FIG. 12, a weighted sum $S_j$ may be computed as a summation of N terms with index i. The N terms may each include the scalar product of a weighting coefficient $w_i$ and a difference value $X_i$ (e.g., difference between a metric of step 1204 and a reference value). For example, a patient monitoring system may compute a weighted sum of the changes in pulse rate 1210, DPTT 1212, pulse wave area 1214, pulse moment 1216 (e.g., of any suitable order), and PPG signal baseline offset 1218.

Illustrative step 1270 of FIG. 12 may include comparing the composite metric of step 1250 to a threshold value. If a patient monitoring system determines that the weighted sum S is greater than a threshold, the patient monitoring system may, for example, recalibrate a device (e.g., a CNIBP device), initiate a NIBP device measurements (e.g., a cuff inflation), store an event marker, trigger a response (e.g., an alarm), perform any other suitable function, or any combination thereof. In some embodiments, a determination that S is greater than a threshold may coincide with the occurrence of a physiological event.

Although shown as ">" in step 1270 of FIG. 12, the inequity symbol may also be included as "<" in some embodiments. For example, in some embodiments, weighted sum S and the threshold of step 1270 may be negative valued. When both weighted sum S and the threshold are negative valued, larger changes relative to the reference values used to compute S are denoted by more negative values of S, characterized by a "<" inequality symbol. In some embodiments, the absolute value of S may be computed and compared with a threshold. Any suitable mathematical manipulations may be used to determine S, and compare S with a suitable threshold. In some embodiments, a reference value may be zero. For example, a metric value may be compared directly with a threshold because the difference between the metric value and a reference value of zero is identically the metric value.

What is claimed is:

1. A method for monitoring blood pressure (BP), the method comprising:
   (a) determining, by a processor, a current BP measurement using a non-invasive blood pressure (NIBP) device;
   (b) associating, by the processor, a first reference metric value and a second reference metric value with the current BP measurement, wherein the first reference metric value is based at least in part on a reference pulse rate, and wherein the second reference metric value is at least one of a reference differential pulse transit time (DPTT), a reference pulse moment, and a reference photoplethysmograph (PPG) baseline offset;
   (c) monitoring, by the processor, a first metric value and a second metric value based at least in part on a continuous non-invasive technique, wherein the first monitored metric value is based at least in part on pulse rate, and wherein the second monitored metric value is at least one of DPTT, pulse moment and PPG baseline offset;
   (d) computing, by the processor, a first difference based at least in part on the first monitored metric value and the first reference metric value;
   (e) computing, by the processor, a second difference based at least in part on the second monitored metric value and the second reference metric value;
   (f) computing, by the processor, a composite metric based on the first difference and the second difference;
   (g) updating, by the processor, the current BP measurement using the NIBP device when the composite metric exceeds a threshold;
   (h) determining, by the processor, at least one calibration coefficient of a photoplethysmography based non-invasive blood pressure (PNIBP) calculation formula when the composite metric exceeds the threshold; and
   (i) determining, by the processor, a physiological parameter using a device that is calibrated using the at least one calibration coefficient.

2. The method of claim 1, wherein the first metric value is based at least in part on pulse rate, DPTT, and one or more of pulse wave area, pulse statistical moment, pulse wave centroid, rotational moments, pulse wave fiducial positions, and DC offset.

3. The method of claim 1, wherein the threshold is based at least in part on the current blood pressure measurement.

4. The method of claim 1, wherein the threshold is based on the first monitored metric value.

5. The method of claim 1, wherein the threshold value is based at least in part on the relative magnitudes of the first monitored metric value and the first reference metric value.

6. The method of claim 1, wherein the threshold is based at least in part on user input.

7. The method of claim 1, wherein the first monitored metric value is based at least in part on a photoplethysmograph (PPG) signal.

8. The method of claim 1, wherein computing the first difference further comprises computing a difference based at least in part on pulse rate, and two or more of DPPT, signal derivative, pulse wave area, notch position, pulse moment, and PPG baseline offset.

9. The method of claim 1, further comprising measuring a change in the first monitored metric value, wherein computing the first difference based at least in part on the first monitored metric value and the first reference metric value is further based at least in part on the change in the first monitored metric value.

10. The method of claim 1, further comprising repeating steps (a) through (i) at least once upon completing step (i).

11. A system for monitoring blood pressure (BP), the system comprising:
 at least one sensing device;
 a signal input configured to receive at least one physiological signal of a subject from the at least one sensing device;
 a non-invasive blood pressure (NIBP) device; and
 a processor coupled to the signal input and to the NIBP device and configured to:
  (a) determine a current BP measurement using the NIBP device;
  (b) associate a first reference metric value and a second reference metric value with the current BP measurement based at least in part on the at least one physiological signal, wherein the first reference metric value is based at least in part on a reference pulse rate and the second reference metric value is at least one of a reference differential pulse transit time (DPTT), a reference pulse moment, and a reference photoplethysmograph (PPG) baseline offset;
  c) monitor a first metric value and a second metric value based at least in part on a continuous noninvasive technique and on the at least one physiological signal, wherein the first monitored metric value is based at least in part on pulse rate and the second monitored metric value is at least one of DPTT, pulse moment, and PPG baseline offset;
  (d) compute a first difference based at least in part on the first monitored metric value and the first reference metric value;
  (e) compute a second difference based at least in part on the second monitored metric value and the second reference metric value;
  (f) compute a composite metric based on the first difference and the second difference;
  (g) update the current BP measurement using the NIBP device when the composite metric exceeds a threshold;
  (h) determine at least one calibration coefficient of a photoplethysmography based non-invasive blood pressure (PNIBP) calculation formula when the composite metric exceeds the threshold; and
  (i) determine a physiological parameter using a device that is calibrated using the at least one calibration coefficient.

12. The system of claim 11, wherein the processor is further configured to compute the threshold value.

13. The system of claim 11, wherein the processors is further configured to receive user input, wherein the threshold value is determined based at least in part on user input.

14. The system of claim 11, wherein the threshold is based on the first monitored metric value.

15. The system of claim 11, wherein the threshold value is based at least in part on the relative magnitudes of the first monitored metric value and the first reference metric value.

16. The system of claim 11, wherein the processor is further configured to compute the first difference based at least in part on pulse rate, and two or more of DPPT, signal derivative, pulse wave area, notch position, pulse moment, and PPG baseline offset.

17. The system of claim 11, wherein the processor is further configured to measure a change in the first monitored metric value, wherein the first difference is further based at least in part on the change in the first monitored metric value.

18. The system of claim 11, wherein the at least one sensing device comprises a photoplethysmograph (PPG) sensor.

19. The system of claim 11, wherein the processor is further configured to repeat steps (a) through (i) at least once upon completing step (i).

20. The system of claim 11, wherein the at least one sensing device comprises two PPG sensors.

* * * * *